(12) United States Patent
Merianos et al.

(10) Patent No.: US 8,519,010 B2
(45) Date of Patent: *Aug. 27, 2013

(54) ANTIMICROBIAL COMPOSITIONS

(75) Inventors: John J. Merianos, Middletown, NJ (US); Paul Garelick, South Plainfield, NJ (US); Susan M. Lindstrom, Ramsey, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/097,281

(22) Filed: Apr. 29, 2011

(65) Prior Publication Data
US 2011/0207787 A1    Aug. 25, 2011

Related U.S. Application Data

(63) Continuation of application No. 10/820,349, filed on Apr. 8, 2004, now Pat. No. 7,935,732.

(51) Int. Cl.
*A01N 31/00* (2006.01)

(52) U.S. Cl.
USPC ........... 514/738; 514/375; 514/479; 514/769; 514/772; 514/772.4; 514/789

(58) Field of Classification Search
USPC .............. 514/738, 375, 479, 769, 772, 772.4, 514/789
See application file for complete search history.

(56) References Cited

U.S. PATENT DOCUMENTS
7,935,732 B2 * 5/2011 Merianos et al. ............. 514/738

FOREIGN PATENT DOCUMENTS
JP    10053510 A  *  2/1998

OTHER PUBLICATIONS
Enclosed English-abstract of JP 10053510 A, Abe et al. (1998).*

* cited by examiner

*Primary Examiner* — Kevin E Weddington
(74) *Attorney, Agent, or Firm* — William J. Davis; Thompson Hine LLP

(57) ABSTRACT

What is described herein are antimicrobial compositions which are defined blends of a 1,2-diol and phenoxyethanol which show broad activity against bacteria, fungi and mold spores. This activity is potentiated by the addition thereto of small amounts of a co-biocide for which the blend acts as a delivery system for the otherwise water-insoluble co-biocide.

14 Claims, No Drawings

ANTIMICROBIAL COMPOSITIONS

CROSS REFERENCE TO RELATED APPLICATION

This application is a continuation of U.S. application Ser. No. 10/820,349 filed Apr. 8, 2004, the entire contents of which are hereby incorporated by reference.

BACKGROUND OF THE INVENTION

1. Field of the Invention

This invention relates to antimicrobial compositions, and, more particularly, to a defined blend of a 1,2-diol and phenoxyethanol, optionally with a co-biocide, which compositions show broad activity against bacteria, fungi and mold spores.

2. Description of the Prior Art

Personal care products come in many different forms. They include creams, lotions, pastes, liquids, aerosols, shampoos, gels, wipes, bars, sticks, powders and granules any or all of which are intended for topical application to the skin including the scalp and the mucosa including the lips.

The products are generally designed to have a substantial shelf life. The products need to be manufactured at one site, transported possibly over a considerable distance to a depot or other storage facility prior to further transport to a point of sale. The product may then spend considerable time on a retailer's shelf prior to purchase and further storage by the user whether for individual use or use in, for example, a hotel, workplace, institution or the like. All of such storage will take place under uncontrolled conditions including considerable variation in temperature.

In order to keep bacterial and fungal growth in such products at an acceptable level it is conventional practice for the products to contain a preservative. Many preservatives are available. The appropriate preservative has to be selected with regard to its efficacy and its acceptability to contact with human or animal skin. With regard to its acceptability there are in many countries laws and regulations governing the maximum permitted content of preservative in products intended for human use due to their possible toxic or otherwise harmful effect.

The need to control microbiological growth in personal care products is known to be particularly acute in water based products such as non-ionic oil-in-water emulsions and in pre-impregnated wipes such as baby wipes.

For example, U.S. Pat. No. 6,607,738 described a preservative system of iodopropynyl butyl carbamate (IPBC) and phenoxyethanol (PE) in a weight ratio of 1:90 to 1:400 for use in personal care products.

U.S. Pat. No. 5,516,510 also disclosed deodorizing active ingredients to reduce the unpleasant odor caused by microorganisms which comprised a glycerin monoalkyl ether in combination with an astringent and/or a naturally occurring deodorant.

EP 1206933 described a preservative composition of caprylyl glycol (1,2-octanediol) and iodopropynyl butyl carbamate in a weight ratio of 0.1 to 500.

U.S. Pat. No. 5,733,362 was directed to a bacterial composition of 2-methyl-4,5-trimethylene-4-isothiazoline-3-on; 3-iodo-2-propynyl butyl carbamate and 2-phenoxyethanol.

EP 1238651 described that the activity of preservative mixtures of iodopropynyl butyl carbamate and phenoxyethanol, in a weight ratio of 1:90 to 1:200, preferably 1:100, can be potentiated by adding caprylyl glycol thereto, in a weight ratio of the latter to the mixture of 0.1 to 500, preferably 1:55.

Thus the formulation of caprylyl glycol, iodopropynyl butyl carbamate and phenoxyethanol had weight ratios of each of 55:1:100 to 200:1:400, respectively. The personal care formulations contained 0.1-30% caprylyl glycol, preferably 0.5%; with 0.001-1% IPBC, preferably 0.001-0.01%; and with phenoxyethanol of 0.1-3%, preferably 0.5-1%.

JP Application No. 11045504 described an antiseptic microbicide and compositions thereof which contained a 1,2-alkane diol. These compositions effectively reduced the required dosage of conventional antiseptic microbicides such as paraben, benzoic acid and the like. The 1,2-alkane diol therein could be blended with a photosensitizer, benzoic acid or its salt, phenoxyethanol or 4-isopropyl-3-methylphenol. However, there was no disclosure of suitable blends of 1,2-alkane diol and phenoxyethanol at predetermined weight ratios and HLB values, which could deliver water insoluble biocides such as IPBC into aqueous personal care systems at a relatively high concentration of such biocides.

These and other prior art references in this field were concerned with the problem that many are antibacterials such as IPBC have limited aqueous solubility in personal care systems; particularly at the high concentrations necessary for effective antimicrobial activity. Thus, at very low concentrations they remain in solution but do not contribute as much activity as desired for these products.

Accordingly, it is desired to provide a blend of 1,2-diol and phenoxyethanol at a predetermined ratio and HLB value which can deliver water insoluble biocides into an aqueous personal care system at relatively high concentrations thereby providing more effective preservative activity in such systems.

SUMMARY OF THE INVENTION

What is described herein is an antimicrobial composition which is active against bacteria, yeast and mold spores, consisting essentially of, by wt.

(a) 40-60% of a 1,2-diol selected from the group consisting of 1,2-pentanediol, 1,2-hexanediol and 1,2-octanediol;

(b) 40-60% of phenoxyethanol; and (c) 0-10% of a co-biocide selected from the group consisting of sorbic acid, benzoic acid, dibromodicyanobutane, iodopropynyl butyl carbamate and 1,2-benzisothiazolin-3-one.

A preferred antimicrobial composition of the invention includes (c) sorbic acid and/or 1% iodopropynyl butyl carbamate.

Most preferred antimicrobial compositions herein are those wherein (a) is about 44% and (b) is about 56%.

Also preferred are antimicrobial compositions wherein (c) is sorbic acid present in an amount of about 5-7% of the composition, or IPBC present in an amount of 1.25-1.50%.

Preferred antimicrobial compositions of the invention include those wherein (a) is 41-42%, (b) is 52-53%; and (c) is sorbic acid 5-7%; and (a) is 43.3; (b) is 55.3; and (c) is IPBC 1.4%.

The invention also encompasses personal care products which include the antimicrobial composition described above, preferably wherein the antibacterial composition is present in an amount of 0.1-2% by weight of the product, most preferably 0.5-1.5%.

DETAILED DESCRIPTION OF THE INVENTION

In accordance with the invention, there is provided herein an antimicrobial composition which is active against bacteria, yeast and mold spores, consisting essentially of, by wt.

(a) 40-60% of a 1,2-diol selected from the group consisting of 1,2-pentanediol, 1,2-hexanediol and 1,2-octanediol;

(b) 40-60% of phenoxyethanol; and (c) 0-10% of a co-biocide selected from the group consisting of sorbic acid, benzoic acid, dibromodicyanobutane, iodopropynyl butyl carbamate and 1,2-benzisothiazolin-3-one.

Preferably the antimicrobial composition includes (c) sorbic acid and/or 1% iodopropynyl butyl carbamate.

Most preferably, the antimicrobial composition includes (a) about 44% and (b) about 56%, and, optionally, (c) is sorbic acid, present in an amount of about 5-7% of the composition, or (c) is IPBC present in an amount of 1.25-1.50%.

Most preferably, it is an antimicrobial composition wherein (a) is 41-42%, (b) is 52-53%; and (c) is sorbic acid 5-7%; most preferably, wherein (a) is 43.3; (b) is 55.3; and (c) is IPBC 1.4%.

Personal care products particularly utilize the antimicrobial composition, preferably, wherein the antibacterial composition is present in an amount of 0.1-2% by weight of the product, most preferably, 0.5-1.5%.

The invention will now be described in more detail by the following challenge test examples on the invention formulations.

Example 1

| ANTIMICROBIAL: 1,2-Octanediol/Phenoxyethanol (40/60 wt. ratio) PRODUCT BASE: Screening emulsion (Standard Emulsion) | | | | |
|---|---|---|---|---|
| TEST ORGANISMS | INOCULUM (0 hours) | REINOCULUM (21 days) | | |
| Staph aureus 6538 | $1.9 \times 10^6$ cfu/ml | $1.2 \times 10^6$ cfu/ml | | |
| E. coli 8739 | $4.6 \times 10^6$ cfu/ml | $2.1 \times 10^6$ cfu/ml | | |
| P. aeruginosa 9027 | $1.7 \times 10^6$ cfu/ml | $2.1 \times 10^6$ cfu/ml | | |
| B. cepacia 25416 | $2.5 \times 10^6$ cfu/ml | $2.0 \times 10^6$ cfu/ml | | |
| C. albicans 10231 | $2.7 \times 10^6$ cfu/ml | $9.0 \times 10^5$ cfu/ml | | |
| A. niger 16404 | $3.0 \times 10^5$ cfu/ml | $1.0 \times 10^5$ cfu/ml | | |
| TEST ORGANISMS | ASSAY INTERVALS | | | |
|  | 48 HRS | 7 D | 14 D | 21 D | 28 D |
| USE LEVEL: 0.5% | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 2.2E5 | <10 | <10 | <10 | <10 |
| A. niger 16404 | 5.5E5 | 2E4 | 3.8E2 | 6E1 | 6.6E3 |
| USE LEVEL: 1.0% | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 1.4E5 | <10 | <10 | <10 | <10 |

Example 2

| ANTIMICROBIAL: 1,2-Octanediol/Phenoxyethanol (40/60) PRODUCT BASE: Nonionic emulsion | | | | |
|---|---|---|---|---|
| TEST ORGANISMS | INOCULUM (0 hours) | REINOCULUM (21 days) | | |
| Staph aureus 6538 | $1.3 \times 10^6$ cfu/ml | $8.0 \times 10^6$ cfu/ml | | |
| E. coli 8739 | $3.9 \times 10^6$ cfu/ml | $4.8 \times 10^6$ cfu/ml | | |
| P. aeruginosa 9027 | $2.5 \times 10^6$ cfu/ml | $4.7 \times 10^6$ cfu/ml | | |
| B. cepacia 25416 | $1.5 \times 10^6$ cfu/ml | $1.0 \times 10^6$ cfu/ml | | |
| C. albicans 10231 | $3.2 \times 10^6$ cfu/ml | $1.6 \times 10^6$ cfu/ml | | |
| A. niger 16404 | $4.0 \times 10^5$ cfu/ml | $2.6 \times 10^5$ cfu/ml | | |
| TEST ORGANISMS | ASSAY INTERVALS | | | |
|  | 48 HRS | 7 D | 14 D | 21 D | 28 D |
| USE LEVEL: 0.5% | | | | |
| Staph. aureus 6538 | 1.4E5 | <10 | <10 | <10 | <10 |
| E. coli 8739 | 6.6E3 | <10 | <10 | <10 | <10 |
| P. aeruginosa 9027 | <10 | <10 | <10 | <10 | <10 |
| B. cepacia 25416 | 4.0E4 | <10 | <10 | <10 | <10 |
| C. albicans 10231 | >1E6 | 8.1E5 | 5.2E4 | <10 | >1E4 |
| A. niger 16404 | 5.9E5 | 1.9E5 | 3.5E4 | 1.2E4 | 6.9E5 |
| USE LEVEL: 1.0% | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 3.4E5 | <10 | <10 | <10 | <10 |
| A. niger 16404 | 6.5E5 | 2.4E4 | 1.2E3 | 9E1 | >1E4 |

Example 3

| ANTIMICROBIAL: 1,2-Octanediol/Phenoxyethanol (40/60)/1.5% BIT PRODUCT BASE: Screening Emulsion | | | | |
|---|---|---|---|---|
| TEST ORGANISMS | INOCULUM (0 hours) | REINOCULUM (21 days) | | |
| Staph aureus 6538 | $4.9 \times 10^6$ cfu/ml | $2.6 \times 10^6$ cfu/ml | | |
| E. coli 8739 | $5.6 \times 10^6$ cfu/ml | $4.3 \times 10^6$ cfu/ml | | |
| P. aeruginosa 9027 | $3.1 \times 10^6$ cfu/ml | $3.2 \times 10^6$ cfu/ml | | |
| B. cepacia 25416 | $2.7 \times 10^6$ cfu/ml | $1.8 \times 10^6$ cfu/ml | | |
| C. albicans 10231 | $4.2 \times 10^6$ cfu/ml | $1.7 \times 10^7$ cfu/ml | | |
| A. niger 16404 | $1.9 \times 10^5$ cfu/ml | $4.0 \times 10^5$ cfu/ml | | |
| TEST ORGANISMS | ASSAY INTERVALS | | | |
|  | 48 HRS | 7 D | 14 D | 21 D | 28 D |
| USE LEVEL: 0.67% (100 ppm BIT) | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |
| USE LEVEL: 1.33% (200 ppm BIT) | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

Example 4

| ANTIMICROBIAL: 1,2-Octanediol/Phenoxyethanol (40/60)/1.5% BIT PRODUCT BASE: Nonionic Emulsion | | |
|---|---|---|
| TEST ORGANISMS | INOCULUM (0 hours) | REINOCULUM (21 days) |
| Staph aureus 6538 | $1.2 \times 10^6$ cfu/ml | $3.7 \times 10^6$ cfu/ml |
| E. coli 8739 | $3.2 \times 10^6$ cfu/ml | $3.1 \times 10^6$ cfu/ml |
| P. aeruginosa 9027 | $3.0 \times 10^6$ cfu/ml | $4.6 \times 10^6$ cfu/ml |
| B. cepacia 25416 | $6.0 \times 10^5$ cfu/ml | $3.2 \times 10^6$ cfu/ml |
| C. albicans 10231 | $2.8 \times 10^6$ cfu/ml | $2.4 \times 10^6$ cfu/mml |
| A. niger 16404 | $7.0 \times 10^5$ cfu/ml | $4.0 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.67% (100 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 3E1 | <10 | <10 | <10 | <10 |
| USE LEVEL: 1.33% (200 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

Example 5

| ANTIMICROBIAL: 1,2-Octanediol/Phenoxyethanol (40/60)/1.5% BIT PRODUCT BASE: Screening Emulsion | | |
|---|---|---|
| TEST ORGANISMS | INOCULUM (0 hours) | REINOCULUM (21 days) |
| Staph aureus 6538 | $3.7 \times 10^6$ cfu/ml | $2.9 \times 10^6$ cfu/ml |
| E. coli 8739 | $3.1 \times 10^6$ cfu/ml | $5.4 \times 10^6$ cfu/ml |
| P. aeruginosa 9027 | $4.6 \times 10^6$ cfu/ml | $3.8 \times 10^6$ cfu/ml |
| B. cepacia 25416 | $3.2 \times 10^6$ cfu/ml | $2.9 \times 10^6$ cfu/ml |
| C. albicans 10231 | $2.4 \times 10^6$ cfu/ml | $2.2 \times 10^6$ cfu/ml |
| A. niger 16404 | $4.0 \times 10^5$ cfu/ml | $2.9 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.25% (37.5 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 7.1E2 | <10 | <10 | <10 | <10 |
| A. niger 16404 | 4.2E4 | 3.4E3 | 1.2E2 | 2E1 | 6.7E2 |
| USE LEVEL: 0.5% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | 2E1 (replate <10) |

Example 6

| ANTIMICROBIAL: 1,2-Octanediol/Phenoxyethanol (40/60)/1.5% BIT PRODUCT BASE: Nonionic Emulsion | | |
|---|---|---|
| TEST ORGANISMS | INOCULUM (0 hours) | REINOCULUM (21 days) |
| Staph aureus 6538 | $4.9 \times 10^6$ cfu/ml | $4.8 \times 10^6$ cfu/ml |
| E. coli 8739 | $3.5 \times 10^6$ cfu/ml | $3.1 \times 10^6$ cfu/ml |
| P. aeruginosa 9027 | $4.0 \times 10^6$ cfu/ml | $3.0 \times 10^6$ cfu/ml |
| B. cepacia 25416 | $4.0 \times 10^6$ cfu/ml | $2.2 \times 10^6$ cfu/ml |
| C. albicans 10231 | $3.5 \times 10^6$ cfu/ml | $8.0 \times 10^5$ cfu/ml |
| A. niger 16404 | $2.7 \times 10^6$ cfu/ml | $1.8 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.25% (37.5 ppm BIT) | | | | | |
| Staph. aureus 6538 | 2E1 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | 2E1 | <10 | <10 | <10 | <10 |
| C. albicans 10231 | >1E6 | 7.2E2 | 1E2 | <10 | >1E4 |
| A. niger 16404 | 3.9E5 | 2.4E5 | 1.9E5 | 1.6E5 | 2.5E5 |
| USE LEVEL: 0.50% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 4.4E4 | 2E3 | 5E1 | <10 | 3.5E3 |

Example 7

| ANTIMICROBIAL: 1,2-Octanediol/Phenoxyethanol (40/60)/1.5% BIT PRODUCT BASE: Screening Emulsion | | |
|---|---|---|
| TEST ORGANISMS | INOCULUM (0 hours) | REINOCULUM (21 days) |
| Staph aureus 6538 | $3.6 \times 10^6$ cfu/ml | $2.8 \times 10^6$ cfu/ml |
| E. coli 8739 | $5.8 \times 10^6$ cfu/ml | $3.5 \times 10^6$ cfu/ml |
| P. aeruginosa 9027 | $4.0 \times 10^6$ cfu/ml | $3.2 \times 10^6$ cfu/ml |
| B. cepacia 25416 | $3.0 \times 10^6$ cfu/ml | $1.8 \times 10^6$ cfu/ml |
| C. albicans 10231 | $2.7 \times 10^6$ cfu/ml | $1.7 \times 10^6$ cfu/ml |
| A. niger 16404 | $1.3 \times 10^6$ cfu/ml | $4.9 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.50% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |
| USE LEVEL: 0.67% (100 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

Example 8

| ANTIMICROBIAL: 1,2-Octanediol/Phenoxyethanol (40/60)/2.5% BIT PRODUCT BASE: Screening Emulsion | | | | | |
|---|---|---|---|---|---|
| TEST ORGANISMS | INOCULUM (0 hours) | | REINOCULUM (21 days) | | |
| Staph aureus 6538 | $3.6 \times 10^6$ cfu/ml | | $2.8 \times 10^6$ cfu/ml | | |
| E. coli 8739 | $5.8 \times 10^6$ cfu/ml | | $3.5 \times 10^6$ cfu/ml | | |
| P. aeruginosa 9027 | $4.0 \times 10^6$ cfu/mml | | $3.2 \times 10^6$ cfu/ml | | |
| B. cepacia 25416 | $3.0 \times 10^6$ cfu/ml | | $1.8 \times 10^6$ cfu/ml | | |
| C. albicans 10231 | $2.7 \times 10^6$ cfu/ml | | $1.7 \times 10^6$ cfu/ml | | |
| A. niger 16404 | $1.3 \times 10^6$ cfu/ml | | $4.9 \times 10^5$ cfu/ml | | |
| TEST ORGANISMS | ASSAY INTERVALS | | | | |
| | 48 HRS | 7 D | 14 D | 21 D | 28 D |
| USE LEVEL: 0.3% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 5.8E3 | 2E1 | <10 | <10 | <10 |
| A. niger 16404 | 1.8E2 | <10 | <10 | <10 | <10 |
| USE LEVEL: 0.4% (100 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

Example 9

| ANTIMICROBIAL: 1,2-Octanediol/Phenoxyethanol (40/60)/1.5% BIT PRODUCT BASE: Nonionic Emulsion | | | | | |
|---|---|---|---|---|---|
| TEST ORGANISMS | INOCULUM (0 hours) | | REINOCULUM (21 days) | | |
| Staph aureus 6538 | $3.0 \times 10^6$ cfu/ml | | $2.8 \times 10^6$ cfu/ml | | |
| E. coli 8739 | $5.8 \times 10^6$ cfu/ml | | $3.5 \times 10^6$ cfu/ml | | |
| P. aeruginosa 9027 | $4.0 \times 10^6$ cfu/ml | | $3.2 \times 10^6$ cfu/ml | | |
| B. cepacia 25416 | $3.0 \times 10^6$ cfu/ml | | $1.8 \times 10^6$ cfu/ml | | |
| C. albicans 10231 | $2.7 \times 10^6$ cfu/ml | | $1.7 \times 10^6$ cfu/ml | | |
| A. niger 16404 | $1.3 \times 10^6$ cfu/ml | | $4.9 \times 10^5$ cfu/ml | | |
| TEST ORGANISMS | ASSAY INTERVALS | | | | |
| | 48 HRS | 7 D | 14 D | 21 D | 28 D |
| USE LEVEL: 0.50% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 8E1 | <10 | <10 | <10 | <10 |
| USE LEVEL: 0.67% (100 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

Example 10

| ANTIMICROBIAL: 1,2-Octanediol/Phenoxyethanol (40/60)/2.5% BIT PRODUCT BASE: Nonionic Emulsion | | | | | |
|---|---|---|---|---|---|
| TEST ORGANISMS | INOCULUM (0 hours) | | REINOCULUM (21 days) | | |
| Staph aureus 6538 | $3.0 \times 10^6$ cfu/ml | | $2.8 \times 10^6$ cfu/ml | | |
| E. coli 8739 | $5.8 \times 10^6$ cfu/ml | | $3.5 \times 10^6$ cfu/ml | | |
| P. aeruginosa 9027 | $4.0 \times 10^6$ cfu/ml | | $3.2 \times 10^6$ cfu/ml | | |
| B. cepacia 25416 | $2.7 \times 10^6$ cfu/ml | | $1.8 \times 10^6$ cfu/ml | | |
| C. albicans 10231 | $2.7 \times 10^6$ cfu/ml | | $1.7 \times 10^6$ cfu/ml | | |
| A. niger 16404 | $1.3 \times 10^6$ cfu/ml | | $4.9 \times 10^5$ cfu/ml | | |
| TEST ORGANISMS | ASSAY INTERVALS | | | | |
| | 48 HRS | 7 D | 14 D | 21 D | 28 D |
| USE LEVEL: 0.30% (75 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 1E4 | 8.6E2 | 2.1E2 | 3E1 | 8.3E2 |
| USE LEVEL: 0.40% (100 ppm BIT) | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 1E1 | <10 | <10 | <10 | <10 |

Example 11

| ANTIMICROBIAL: 1,2-Octanediol/Phenoxyethanol (40/60), 6% sorbic acid PRODUCT BASE: Nonionic Emulsion | | | | | |
|---|---|---|---|---|---|
| TEST ORGANISMS | INOCULUM (0 hours) | | REINOCULUM (21 days) | | |
| Staph aureus 6538 | $1.3 \times 10^6$ cfu/ml | | $8.0 \times 10^6$ cfu/ml | | |
| E. coli 8739 | $3.9 \times 10^6$ cfu/ml | | $4.8 \times 10^6$ cfu/ml | | |
| P. aeruginosa 9027 | $2.5 \times 10^6$ cfu/ml | | $4.7 \times 10^6$ cfu/ml | | |
| B. cepacia 25416 | $1.5 \times 10^6$ cfu/ml | | $1.0 \times 10^6$ cfu/ml | | |
| C. albicans 10231 | $3.2 \times 10^6$ cfu/ml | | $1.6 \times 10^6$ cfu/ml | | |
| A. niger 16404 | $4.0 \times 10^5$ cfu/ml | | $2.6 \times 10^5$ cfu/ml | | |
| TEST ORGANISMS | ASSAY INTERVALS | | | | |
| | 48 HRS | 7 D | 14 D | 21 D | 28 D |
| USE LEVEL: 0.5% | | | | | |
| Staph. aureus 6538 | 1.1E2 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | 8E3 | 7E4 | 1.1E5 |
| C. albicans 10231 | >1E6 | 3.1E4 | <10 | <10 | >1E4 |
| A. niger 16404 | 8.3E5 | 4E1 | <10 | <10 | 1E1 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |

| ANTIMICROBIAL: 1,2-Octanediol/Phenoxyethanol (40/60), 6% sorbic acid PRODUCT BASE: Nonionic Emulsion | | | | |
|---|---|---|---|---|
| C. albicans 10231 | 1.2E4 | <10 | <10 | <10 | <10 |
| A. niger 16404 | 3E5 | <10 | <10 | <10 | <10 |

Example 12

| ANTIMICROBIAL: 1,2-Octanediol/Phenoxyethanol (40/60), 6% sorbic acid PRODUCT BASE: Nonionic Emulsion | | |
|---|---|---|
| TEST ORGANISMS | INOCULUM (0 hours) | REINOCULUM (21 days) |
| Staph aureus 6538 | $6.9 \times 10^6$ cfu/ml | $1.8 \times 10^6$ cfu/ml |
| E. coli 8739 | $7.8 \times 10^6$ cfu/ml | $3.5 \times 10^6$ cfu/ml |
| P. aeruginosa 9027 | $5.1 \times 10^6$ cfu/ml | $1.3 \times 10^6$ cfu/ml |
| B. cepacia 25416 | $2.2 \times 10^6$ cfu/ml | $7.0 \times 10^6$ cfu/ml |
| C. albicans 10231 | $3.7 \times 10^6$ cfu/ml | $6.0 \times 10^7$ cfu/ml |
| A. niger 16404 | $1.8 \times 10^5$ cfu/ml | $8.0 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.50% | | | | | |
| Staph. aureus 6538 | 1E1 | <10 | <10 | <10 | <10 |
| E. coli 8739 | 6E1 | <10 | <10 | <10 | <10 |
| P. aeruginosa 9027 | 1E2 | <10 | <10 | <10 | <10 |
| B. cepacia 25416 | 5.8E4 | <10 | <10 | <10 | <10 |
| C. albicans 10231 | >1E6 | 1.7E5 | 2E1 | <10 | >1E4 |
| A. niger 16404 | 1E5 | 5.8E4 | 3E4 | 6E3 | 3.9E5 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 3E4 | <10 | <10 | <10 | <10 |

Example 13

| ANTIMICROBIAL: 1,2-Octanediol/Phenoxyethanol (40/60), 6% sorbic acid PRODUCT BASE: Nonionic Emulsion | | |
|---|---|---|
| TEST ORGANISMS | INOCULUM (0 hours) | REINOCULUM (21 days) |
| Staph aureus 6538 | $6.9 \times 10^6$ cfu/ml | $1.8 \times 10^6$ cfu/ml |
| E. coli 8739 | $7.8 \times 10^6$ cfu/ml | $3.5 \times 10^6$ cfu/ml |
| P. aeruginosa 9027 | $5.1 \times 10^6$ cfu/ml | $1.3 \times 10^6$ cfu/ml |
| B. cepacia 25416 | $2.2 \times 10^6$ cfu/ml | $7.0 \times 10^6$ cfu/ml |
| C. albicans 10231 | $3.7 \times 10^6$ cfu/ml | $6.0 \times 10^7$ cfu/ml |
| A. niger 16404 | $1.8 \times 10^5$ cfu/ml | $8.0 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.5% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | 8E1 | <10 | <10 | <10 | 2E1 |
| C. albicans 10231 | >1E6 | 1.4E4 | <10 | <10 | <10 |
| A. niger 16404 | 2.1E5 | 5.5E4 | 8E3 | 3E3 | 3.4E5 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 8E3 | <10 | <10 | <10 | <10 |

Example 14

| ANTIMICROBIAL: 1,2-Octanediol/Phenoxyethanol (40/60), 6% sorbic acid PRODUCT BASE: Nonionic Emulsion | | |
|---|---|---|
| TEST ORGANISMS | INOCULUM (0 hours) | REINOCULUM (21 days) |
| Staph. aureus 6538 | $6.9 \times 10^6$ cfu/ml | $1.8 \times 10^6$ cfu/ml |
| E. coli 8739 | $7.8 \times 10^6$ cfu/ml | $3.5 \times 10^6$ cfu/ml |
| P. aeruginosa 9027 | $5.1 \times 10^6$ cfu/ml | $1.3 \times 10^6$ cfu/ml |
| B. cepacia 25416 | $2.2 \times 10^6$ cfu/ml | $7.0 \times 10^6$ cfu/ml |
| C. albicans 10231 | $3.7 \times 10^6$ cfu/ml | $6.0 \times 10^7$ cfu/ml |
| A. niger 16404 | $1.8 \times 10^5$ cfu/ml | $8.0 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.50% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | >1E6 | 2E4 | <10 | <10 | >1E4 |
| A. niger 16404 | 1.8E5 | 1.1E5 | 1.2E3 | 2E2 | >1E4 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | 6E3 | <10 | <10 | <10 | 7E1 |

Example 15

| ANTIMICROBIAL: 1,2-Octanediol/Phenoxyethanol (40/60) PRODUCT BASE: Screening Emulsion | | |
|---|---|---|
| TEST ORGANISMS | INOCULUM (0 hours) | REINOCULUM (21 days) |
| Staph aureus 6538 | $2.9 \times 10^6$ cfu/ml | $2.5 \times 10^5$ cfu/ml |
| E. coli 8739 | $4.7 \times 10^6$ cfu/ml | $3.4 \times 10^6$ cfu/ml |
| P. aeruginosa 9027 | $4.9 \times 10^6$ cfu/ml | $1.2 \times 10^6$ cfu/ml |
| B. cepacia 25416 | $5.3 \times 10^6$ cfu/ml | $1.1 \times 10^6$ cfu/ml |

-continued

| ANTIMICROBIAL: 1,2-Octanediol/Phenoxyethanol (40/60) PRODUCT BASE: Screening Emulsion | | | | | |
|---|---|---|---|---|---|
| C. albicans 10231 | $1.0 \times 10^6$ cfu/ml | | $1.1 \times 10^6$ cfu/ml | | |
| A. niger 16404 | $7.0 \times 10^5$ cfu/ml | | $4.4 \times 10^5$ cfu/ml | | |

| TEST ORGANISMS | ASSAY INTERVALS | | | | |
|---|---|---|---|---|---|
| | 48 HRS | 7 D | 14 D | 21 D | 28 D |
| USE LEVEL: 0.5% | | | | | |
| Staph. aureus 6538 | 7E1 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | 4E4 | <10 | <10 | <10 | 1E1 |
| A. niger 16404 | 2.3E5 | 2.3E4 | 2.5E2 | 2E1 | >1E4 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <.10 | <10 | <10 |
| C. albicans 10231 | <10 | <10 | <10 | <10 | <10 |
| A. niger 16404 | 3E4 | <10 | <10 | <10 | <10 |

Example 16

| ANTIMICROBIAL: 20 Pentanediol/20 Hexanediol/ 20 Octanediol/40 Phenoxyethanol PRODUCT BASE: Screening Emulsion | | |
|---|---|---|
| TEST ORGANISMS | INOCULUM (0 hours) | REINOCULUM (21 days) |
| Staph aureus 6538 | $2.5 \times 10^6$ cfu/ml | $2.5 \times 10^6$ cfu/ml |
| E. coli 8739 | $6.0 \times 10^6$ cfu/ml | $2.9 \times 10^6$ cfu/ml |
| P. aeruginosa 9027 | $5.7 \times 10^6$ cfu/ml | $2.3 \times 10^6$ cfu/ml |
| B. cepacia 25416 | $3.4 \times 10^6$ cfu/ml | $1.5 \times 10^6$ cfu/ml |
| C. albicans 10231 | $2.9 \times 10^6$ cfu/ml | $1.1 \times 10^6$ cfu/mkl |
| A. niger 16404 | $5.1 \times 10^5$ cfu/ml | $2.8 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.25% | | | | | |
| Staph. aureus 6538 | 1.1E6 | 1.6E3 | <10 | <10 | >1E4 |
| E. coli 8739 | 2E2 | <10 | <10 | <10 | <10 |
| P. aeruginosa 9027 | 3E1 | 3E3 | 4E1 | 1E2 | >1E4 |
| B. cepacia 25416 | >1E6 | >1E6 | 4.3E5 | 1.8E5 | >1E6 |
| C. albicans 10231 | 7.9E5 | 1.2E5 | 4.1E2 | 2.2E2 | >1E4 |
| A. niger 16404 | 1.8E5 | 3.2E5 | 3.3E5 | 1.4E5 | 5.1E5 |
| USE LEVEL: 0.50% | | | | | |
| Staph. aureus 6538 | 9.8E4 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | 2.7E5 | <10 | <10 | <10 | <10 |
| C. albicans 10231 | 3.8E5 | 2E2 | <10 | <10 | 8E1 |
| A. niger 16404 | 2.6E5 | 3.3E5 | 1.7E3 | 8E2 | >1E4 |

Example 17

| ANTIMICROBIAL: 20 Pentanediol/20 Hexanediol/ 20 Octanediol/40 Phenoxyethanol PRODUCT BASE: Nonionic Emulsion | | |
|---|---|---|
| TEST ORGANISMS | INOCULUM (0 hours) | REINOCULUM (21 days) |
| Staph aureus 6538 | $2.5 \times 10^6$ cfu/ml | $2.5 \times 10^6$ cfu/ml |
| E. coli 8739 | $6.0 \times 10^6$ cfu/ml | $2.9 \times 10^6$ cfu/ml |
| P. aeruginosa 9027 | $5.7 \times 10^6$ cfu/ml | $2.3 \times 10^6$ cfu/ml |
| B. cepacia 25416 | $3.4 \times 10^6$ cfu/ml | $1.5 \times 10^6$ cfu/ml |
| C. albicans 10231 | $2.9 \times 10^6$ cfu/ml | $1.1 \times 10^6$ cfu/mkl |
| A. niger 16404 | $5.1 \times 10^5$ cfu/ml | $2.8 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.5% | | | | | |
| Staph. aureus 6538 | 2.6E5 | <10 | <10 | <10 | <10 |
| E. coli 8739 | 2.2E4 | <10 | <10 | <10 | <10 |
| P. aeruginosa 9027 | <10 | <10 | <10 | <10 | <10 |
| B. cepacia 25416 | 2.6E5 | 6E3 | <10 | <10 | 2.9E3 |
| C. albicans 10231 | >1E6 | >1E6 | 4.8E4 | 7.1E2 | 9.3E5 |
| A. niger 16404 | 6.8E5 | 4.8E5 | 1.4E5 | >1E4 | 6.2E5 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | 1E2 | <10 | <10 | <10 | <10 |
| C. albicans 10231 | >1E6 | 2.8E4 | <10 | <10 | <10 |
| A. niger 16404 | 3.8E5 | 3.5E5 | 1.3E4 | 2.9E2 | 5.3E4 |

Example 18

| ANTIMICROBIAL: 20 Pentanediol/20 Hexanediol/ 20 Octanediol/40 Phenoxyethanol PRODUCT BASE: Screening Emulsion | | |
|---|---|---|
| TEST ORGANISMS | INOCULUM (0 hours) | REINOCULUM (21 days) |
| Staph aureus 6538 | $1.8 \times 10^6$ cfu/ml | $1.0 \times 10^6$ cfu/ml |
| E. coli 8739 | $3.5 \times 10^6$ cfu/ml | $3.6 \times 10^6$ cfu/ml |
| P. aeruginosa 9027 | $1.3 \times 10^6$ cfu/ml | $2.9 \times 10^6$ cfu/ml |
| B. cepacia 25416 | $7.0 \times 10^6$ cfu/ml | $3.0 \times 10^6$ cfu/ml |
| C. albicans 10231 | $6.0 \times 10^5$ cfu/ml | $2.1 \times 10^6$ cfu/ml |
| A. niger 16404 | $8.0 \times 10^5$ cfu/ml | $2.8 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 0.5% | | | | | |
| Staph. aureus 6538 | 1.3E4 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | 1.9E5 | <10 | <10 | <10 | <10 |
| C. albicans 10231 | 3E5 | 3.3E3 | <10 | <10 | 9.7E2 |
| A. niger 16404 | 6.8E5 | 6E4 | 3.3E4 | 1.1E4 | 6E4 |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |

-continued

ANTIMICROBIAL: 20 Pentanediol/20 Hexanediol/
20 Octanediol/40 Phenoxyethanol
PRODUCT BASE: Screening Emulsion

| | | | | | |
|---|---|---|---|---|---|
| C. albicans 10231 | 3.8E2 | <10 | <10 | <10 | <10 |
| A. niger 16404 | 4.9E4 | 1.4E4 | 1.7E2 | 1.3E2 | 6.7E3 |

Example 19

ANTIMICROBIAL: 1,2-Octanediol/Phenoxyethanol (40/60), 1.25% IPBC
PRODUCT BASE: Screening Emulsion

| TEST ORGANISMS | INOCULUM (0 hours) | REINOCULUM (21 days) |
|---|---|---|
| Staph aureus 6538 | $3.6 \times 10^6$ cfu/ml | $1.6 \times 10^6$ cfu/ml |
| E. coli 8739 | $4.0 \times 10^6$ cfu/ml | $2.2 \times 10^6$ cfu/ml |
| P. aeruginosa 9027 | $4.4 \times 10^6$ cfu/ml | $1.7 \times 10^6$ cfu/ml |
| B. cepacia 25416 | $3.0 \times 10^6$ cfu/ml | $1.7 \times 10^6$ cfu/ml |
| C. albicans 10231 | $4.2 \times 10^6$ cfu/ml | $9.3 \times 10^5$ cfu/ml |
| A. niger 16404 | $9.0 \times 10^5$ cfu/ml | $2.6 \times 10^5$ cfu/ml |

| TEST ORGANISMS | ASSAY INTERVALS | | | | |
|---|---|---|---|---|---|
| | 48 HRS | 7 D | 14 D | 21 D | 28 D |
| USE LEVEL: 1.0% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |
| USE LEVEL: 1.8% | | | | | |
| Staph. aureus 6538 | <10 | <10 | <10 | <10 | <10 |
| E. coli 8739 | <10 | <10 | <10 | <10 | <10 |
| P. aeruginosa 9027 | <10 | <10 | <10 | <10 | <10 |
| B. cepacia 25416 | <10 | <10 | <10 | <10 | <10 |
| C. albicans 10231 | <10 | <10 | <10 | <10 | <10 |
| A. niger 16404 | <10 | <10 | <10 | <10 | <10 |

What is claimed is:

1. An antimicrobial composition which is active against gram-negative bacteria selected from the group consisting of E. coli and P. aeruginosa, gram-positive Staph aureus bacteria, C. albicans, yeast, B. cepacia and A. niger mold spores, said antimicrobial composition consisting essentially of, by wt.:
  (a) 40-60% of a 1,2-diol selected from the group consisting of 1,2-pentanediol, 1,2-hexanediol, 1,2-octanediol and mixtures thereof,
  (b) 40-60% phenoxyethanol; and
  (c) 0-10% of a co-biocide selected from the group consisting of sorbic acid, benzoic acid, dibromodicyanobutane, and 1,2-benzisothiazolin-3-one.

2. An antimicrobial composition according to claim 1 in which (c) is present and is sorbic acid.

3. An antimicrobial composition according to claim 1 wherein (a) is about 44% and (b) is about 56%.

4. An antimicrobial composition according to claim 2 wherein the sorbic acid is present in an amount of about 5-7% of the composition.

5. An antimicrobial composition of claim 1 wherein (a) is 41-42%, (b) is 52-53%; and (c) is sorbic acid at 5-7%.

6. An antimicrobial composition of claim 1 wherein (a) is present in an amount of 43.3%; (b) is present in an amount of 55.3%; and (c) is present in an amount of 1.4%.

7. An antimicrobial composition consisting essentially of, by weight, based on the total weight of (a) and (b):
  (a) 40-60% of a 1,2-diol selected from the group consisting of 1,2-pentanediol, 1,2-hexanediol, 1,2-octanediol and mixtures thereof;
  (b) 40-60% phenoxyethanol; and
  (c) 0-10% of a co-biocide selected from the group consisting of sorbic acid, benzoic acid, dibromodicyano-butane, 1,2-benzisothiazolin-3-one, and mixtures thereof, wherein said antimicrobial composition is active against at least one of E. coli, Staph aureus, P. aeruginosa, B. cepacia, C. albicans, and A. niger.

8. An antimicrobial composition according to claim 7 in which (c) is present and is sorbic acid.

9. An antimicrobial composition according to claim 8 wherein the sorbic acid is present in an amount of about 5-7% of the composition.

10. An antimicrobial composition according to claim 7 wherein (a) is about 40% and (b) is about 60%.

11. An antimicrobial composition according to claim 10 wherein (a) comprises 1,2-octanediol.

12. An antimicrobial composition according to claim 10 wherein a co-biocide is present.

13. An antimicrobial composition according to claim 12 wherein the co-biocide is sorbic acid.

14. An antimicrobial composition according to claim 13 wherein the sorbic acid is present in an amount of about 5-7%.

* * * * *